United States Patent
Leybaert

(10) Patent No.: US 9,485,983 B2
(45) Date of Patent: Nov. 8, 2016

(54) USE OF CONNEXIN CHANNEL INHIBITORS TO PROTECT GRAFTS

(71) Applicant: Universiteit Gent, Ghent (BE)

(72) Inventor: Luc Leybaert, Bachte-Maria-Leerne (BE)

(73) Assignee: Universiteit Gent, Ghent (BE)

( * ) Notice: Subject to any disclaimer, the term of this patent is extended or adjusted under 35 U.S.C. 154(b) by 11 days.

(21) Appl. No.: 14/650,553

(22) PCT Filed: Dec. 10, 2013

(86) PCT No.: PCT/EP2013/076001
§ 371 (c)(1),
(2) Date: Jun. 8, 2015

(87) PCT Pub. No.: WO2014/095468
PCT Pub. Date: Jun. 26, 2014

(65) Prior Publication Data
US 2015/0313208 A1    Nov. 5, 2015

(30) Foreign Application Priority Data
Dec. 19, 2012   (EP) .................................... 12197955

(51) Int. Cl.
*A01N 1/02*    (2006.01)

(52) U.S. Cl.
CPC ........... *A01N 1/0221* (2013.01); *A01N 1/0226* (2013.01)

(58) Field of Classification Search
CPC ................................................... A01N 1/0221
See application file for complete search history.

(56) References Cited

U.S. PATENT DOCUMENTS

| 6,045,990 A | 4/2000 | Baust et al. |
| 2004/0096813 A1 | 5/2004 | Baust et al. |
| 2008/0132450 A1 | 6/2008 | Lee et al. |

FOREIGN PATENT DOCUMENTS

| WO | 0002572 A1 | 1/2000 |
| WO | 2004046308 A2 | 6/2004 |
| WO | 2008047243 A2 | 4/2008 |
| WO | 2014095468 A1 | 6/2014 |

OTHER PUBLICATIONS

Diestel et al., Methylprednisolone and Tacrolimus Prevent Hypothermia-Induced Endothelial Dysfunction, Journal of Heart and Lung Transplantation, Jul. 1, 2009, pp. 718-724, vol. 28, No. 7.

*Primary Examiner* — Amber D Steele
(74) *Attorney, Agent, or Firm* — TraskBritt, P.C.

(57) ABSTRACT

This disclosure relates to methods to protect grafts against cell death due to preservation of the grafts prior to transplanting these grafts into patients. In particular, this disclosure discloses that connexin channel inhibitors can be used to protect against cell death associated with preservation and temporary storage of cells, tissues and organs. Preservation includes any procedure that involves a lowering of the temperature below the normal body temperature, including hypothermia (cold storage), cryopreservation and vitrification. Grafts that are protected according to this disclosure have an improved biological function.

22 Claims, 2 Drawing Sheets

SEQUENCE LISTING

```
<160> NUMBER OF SEQ ID NOS: 9

<210> SEQ ID NO 1
<211> LENGTH: 11
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa = Ser or Ala
<220> FEATURE:
<221> NAME/KEY: MISC_FEATURE
<222> LOCATION: (2)..(2)
<223> OTHER INFORMATION: Xaa = Arg or Lys
<220> FEATURE:
<221> NAME/KEY: MISC_FEATURE
<222> LOCATION: (7)..(7)
<223> OTHER INFORMATION: Xaa = Thr, Asn or Lys
<220> FEATURE:
<221> NAME/KEY: MISC_FEATURE
<222> LOCATION: (8)..(8)
<223> OTHER INFORMATION: Xaa = Ile or Val
<220> FEATURE:
<221> NAME/KEY: MISC_FEATURE
<222> LOCATION: (10)..(10)
<223> OTHER INFORMATION: Xaa = Ile, Thr, Leu or Met
<220> FEATURE:
<221> NAME/KEY: MISC_FEATURE
<222> LOCATION: (11)..(11)
<223> OTHER INFORMATION: Xaa = Ile, Val, Leu or Tyr

<400> SEQUENCE: 1

Xaa Xaa Pro Thr Glu Lys Xaa Xaa Phe Xaa Xaa
1               5                   10

<210> SEQ ID NO 2
<211> LENGTH: 11
<212> TYPE: PRT
<213> ORGANISM: Homo sapiens

<400> SEQUENCE: 2

Ser Arg Pro Thr Glu Lys Thr Ile Phe Ile Ile
1               5                   10
```

```
<210> SEQ ID NO 3
<211> LENGTH: 13
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa = Val, Ala or Ile
<220> FEATURE:
<221> NAME/KEY: MISC_FEATURE
<222> LOCATION: (3)..(3)
<223> OTHER INFORMATION: Xaa = Tyr or Phe
<220> FEATURE:
<221> NAME/KEY: MISC_FEATURE
<222> LOCATION: (5)..(5)
<223> OTHER INFORMATION: Xaa = Lys, Gln, Ala, Glu, His, Arg, Asn or Asp
<220> FEATURE:
<221> NAME/KEY: MISC_FEATURE
<222> LOCATION: (6)..(6)
<223> OTHER INFORMATION: Xaa = Ser, Ala, Phe or Tyr
<220> FEATURE:
<221> NAME/KEY: MISC_FEATURE
<222> LOCATION: (7)..(7)
<223> OTHER INFORMATION: Xaa = Phe or Ala
<220> FEATURE:
<221> NAME/KEY: MISC_FEATURE
<222> LOCATION: (9)..(9)
<223> OTHER INFORMATION: Xaa = Ile, Val or Leu
<220> FEATURE:
<221> NAME/KEY: MISC_FEATURE
<222> LOCATION: (11)..(11)
<223> OTHER INFORMATION: Xaa = His, Asn or L eu
<220> FEATURE:
<221> NAME/KEY: MISC_FEATURE
<222> LOCATION: (12)..(12)
<223> OTHER INFORMATION: Xaa = Val, Ile or Arg

<400> SEQUENCE: 3

Xaa Cys Xaa Asp Xaa Xaa Xaa Pro Xaa Ser Xaa Xaa Arg
1               5                   10

<210> SEQ ID NO 4
<211> LENGTH: 9
<212> TYPE: PRT
<213> ORGANISM: Homo sapiens

<400> SEQUENCE: 4

Lys Gln Ile Glu Ile Lys Lys Phe Lys
1               5

<210> SEQ ID NO 5
<211> LENGTH: 13
<212> TYPE: PRT
<213> ORGANISM: Homo sapiens

<400> SEQUENCE: 5

Gly His Gly Asp Pro Leu His Leu Glu Glu Val Lys Cys
1               5                   10

<210> SEQ ID NO 6
<211> LENGTH: 10
<212> TYPE: PRT
<213> ORGANISM: Homo sapiens

<400> SEQUENCE: 6

Trp Arg Gln Ala Ala Phe Val Asp Ser Tyr
1               5                   10

<210> SEQ ID NO 7
```

```
<211> LENGTH: 11
<212> TYPE: PRT
<213> ORGANISM: Human immunodeficiency virus

<400> SEQUENCE: 7

Tyr Gly Arg Lys Lys Arg Arg Gln Arg Arg
1               5                   10

<210> SEQ ID NO 8
<211> LENGTH: 16
<212> TYPE: PRT
<213> ORGANISM: Drosophila melanogaster

<400> SEQUENCE: 8

Arg Gln Pro Lys Ile Trp Phe Pro Asn Arg Arg Lys Pro Trp Lys Lys
1               5                   10                  15

<210> SEQ ID NO 9
<211> LENGTH: 10
<212> TYPE: PRT
<213> ORGANISM: Homo sapiens

<400> SEQUENCE: 9

Ser Arg Pro Thr Glu Lys Thr Val Phe Thr
1               5                   10
```

USE OF CONNEXIN CHANNEL INHIBITORS TO PROTECT GRAFTS

CROSS-REFERENCE TO RELATED APPLICATIONS

This application is a national phase entry under 35 U.S.C. §371 of International Patent Application PCT/EP2013/076001, filed Dec. 10, 2013, designating the United States of America and published in English as International Patent Publication WO 2014/095468 A1 on Jun. 26, 2014, which claims the benefit under Article 8 of the Patent Cooperation Treaty and under 35 U.S.C. §119(e) to European Patent Application Serial No. 12197955.3, filed Dec. 19, 2012.

TECHNICAL FIELD

This disclosure generally relates to medicine and biotechnology, and particularly relates to methods to protect grafts against cell death due to preservation of the grafts prior to transplanting these grafts into patients. In particular, this disclosure discloses that connexin channel inhibitors can be used to protect against cell death associated with preservation and temporary storage of cells, tissues and organs. "Preservation" includes any procedure that involves a lowering of the temperature below the normal body temperature, including hypothermia (cold storage), cryopreservation and vitrification. Moreover, grafts that are protected according to this disclosure have an improved biological function.

BACKGROUND

Grafts consisting of entire organs, composite tissues or a collection of cells are often preserved via cold storage, cryopreservation or vitrification before they are transplanted or transferred in animals including humans. Such grafts include entire heart, uterus or kidney (most often kept under hypothermic conditions, e.g., a temperature of 4° C.), composite tissues like fibrocartilage tissue (e.g., meniscus), bone, blood vessels, skin, cornea, nervous tissues, ovarian tissues or embryos (mostly cryopreserved at −80° C., −196° C., or intermediate temperatures), and hematopoietic cells, hepatocytes (liver cells) and oocytes (mostly cryopreserved, some also preserved by the process of vitrification, a procedure that avoids ice crystal formation).

While cooling in general is necessary to preserve some degree of cell viability within the graft, as a result of slowing down all metabolic, signaling and potentially toxic chemical processes, the procedure is intrinsically associated with various degrees of cell stress that may ultimately result in cell damage and cell death. Some chemicals, called "antifreeze" or "cryoprotectants," are commonly used to lower the melting point of water and as such diminish the damage due to freezing. The main goal of adding cryoprotectants is to prevent intracellular ice crystal formation; in most cases, extracellular ice formation is more or less acceptable but intracellular ice formation is to be avoided at all cost. The reason is that ice crystals expel solute and thereby provoke hyperosmolarity in the remaining water solution, leading to water shifts between the intra- and extracellular compartment. Both crystal formation and osmolarity changes are important stress conditions for the cells that negatively influence their viability potential.

Vitrification tries to prevent crystal formation by an extremely fast temperature lowering, thereby limiting water flow and, hence, its availability to be incorporated into crystals. This procedure is ideal for cells, typically for oocytes, but not for organs or composite tissues. In any case, during thawing, re-crystallization can occur (also after vitrification) and this may add additional cell stress. Furthermore, some of the cryoprotectants, e.g., dimethylsulfoxide (DMSO), have intrinsic toxic effects on the graft cells and are known to have adverse effects on specific biological targets.[1-3] Therefore, measures need to be taken that counteract or prevent some of the negative consequences of the cell-stressor conditions associated with cryopreservation or vitrification.

Additionally, hypothermic preservation is also associated with cell stress that relates in the very first place to the presence of an ischemic condition, called cold ischemia. Indeed, hypothermic preservation is mostly used for organs, and because there is no blood flow during preservation, the organ is manifestly in ischemia (the consequence of a compromised/absent perfusion). Ischemia is of particular interest here because it is one of the strong stimuli leading to the opening of connexin and pannexin hemichannels and to the propagation of cell death via gap junction channels (see further). Ischemia is a problem for organs but is less of a problem for thin composite tissues or cells.

In the two latter cases, hypothermia is associated with another stressor: the cooling (without freezing) results in a stronger inhibition of active processes, i.e., high $Q_{10}$ value ATP-consuming processes, as compared to diffusive processes characterized by a $Q_{10}$ close to 1. Thus, major diffusive pathways will still operate while active processes necessary to maintain homeostasis are inhibited. This will result in impaired homeostasis and cell stress. Connexin and pannexin channels (see further) constitute a highly conductant diffusive pathway. Gap junction channels composed of connexins connect the cytoplasm of neighboring cells while hemichannels composed of connexins or pannexins form membrane channels that function as a toxic pore when open. In hypothermia, as well as in cryopreservation and vitrification, ionic and molecular fluxes through these channels may considerably contribute to cell damage. Thus, hypothermia, cryopreservation and vitrification are all associated with particular stressor conditions that inevitably lead to cell dysfunction and cell death.

The case of blood vessel grafts, called vascular grafts, is particularly interesting because these grafts have wide surgical applications, but at the same token, their preservation has faced some of the prototypical problems of cryopreserving composite tissues. These grafts may be preserved by hypothermia, but in most cases, cryopreservation is applied; unfortunately, the latter procedure is still unsatisfactory because of the post-grafting complications of thrombosis and vasospasms that may occur, leading to late graft failure.[4] The risk for thrombosis is enhanced by rejection, leading to loss of endothelial lining and function, and in a later phase, by immune-related intimal hyperplasia and fibrosis.[5] Even with the introduction of immunosuppressive treatment,[6] the improvement of harvesting techniques and preservation fluids,[7] and the use of anticoagulation therapy,[8] the patency of these allografts was not improved in most studies.

The performance of cryopreserved vascular grafts is suboptimal, mainly because of spontaneous vessel wall fractures[9] appearing at the time of thawing or grafting. Another important issue is that the current methods of vascular cryopreservation used in most vascular banks lead to a certain degree of loss of the intimal endothelial layer.[10] Before arterial or venous grafts are implanted to bypass occluded coronary arteries, they undergo extensive apoptotic and necrotic cell death in the intimal and medial layers.[11] Cell death plays an important role in vascular graft failure, and important for the present study, cell-cell communication may act to expand the cell death process to neighboring healthy cells, leading to bystander cell death during cryopreservation and thawing.[12]

The most direct form of cell-cell communication is provided by gap junctions that consist of intercellular channels composed of connexin proteins, named according to their predicted molecular weight.[13] Vascular cells abundantly express connexins, with Cx37, Cx40 and Cx43 as the most representative isoforms.[14] Gap junction channels are formed by the interaction of two hemichannels belonging to the membranes of adjacent cells and directly connect the cytoplasm of neighboring cells. Gap junctions are high-conductance channels that are able to pass cell death messengers leading to bystander cell death.[12] Recently, it has been demonstrated that the physiological messenger inositol 1,4,5 trisphosphate ($IP_3$), which can pass through gap junction channels, becomes a crucial cell death-communicating messenger under pro-apoptotic conditions.[15] Additionally, hemichannels, which are half gap junction channels, may by themselves promote cell death. Unapposed hemichannels in the plasma membrane are typically closed and only open when they become incorporated into a gap junction. However, unapposed hemichannels not assembled into gap junctions may open under certain conditions like cell depolarization, decreased extracellular calcium, changes in intracellular calcium concentration, alterations in phosphorylation or redox status, mechanical strain, and ischemic or inflammatory conditions.[16-20] Hemichannels are non-selective channels that allow, like gap junctions, the passage of up to 1.5 kDa molecules. As a consequence, uncontrolled hemichannel opening may lead to cell death as a toxic pore, caused by excessive diffusive fluxes, most notably the entry of sodium and calcium ions and the loss of cellular ATP or other crucial metabolic molecules.[21-23] Hemichannels can also be composed of pannexins, another class of channel-forming proteins characterized by a membrane topology similar to connexins (but without sequence homology), that, when open, can accelerate or trigger cell death.[24-27]

Gap junction channels and connexin hemichannels can be inhibited by connexin mimetic peptides such as Gap26 and Gap27.[28-30] These peptides are identical to sequences of certain well-defined domains on the extracellular loops of the connexin protein; they first inhibit unapposed hemichannels that have their extracellular loops freely available for peptide interactions, followed by a somewhat delayed inhibition of gap junctions.[22, 31, 32] Previous work has demonstrated that connexin mimetic peptides prevent the propagation of cell death by inhibiting both gap junctions and (unapposed) hemichannels.[22] Recent work has furthermore shown that these peptides can significantly improve the outcome after experimental ischemia applied to heart or brain.[33, 34] In the context of tissue preservation, Xu et al.[35] have recently demonstrated that overexpression of Cx43 can protect cardiomyocytes against cold storage. However, the latter observation is opposite to this disclosure that relates to the block of gap junctions and hemichannels as a way to protect the cells against cell death and cell dysfunction caused by hypothermia or cryopreservation/vitrification and the associated phase of thawing.

Non-peptide inhibitors of connexin channels also exist: these include antibodies directed against the connexin protein and a large class of chemically diverse compounds that non-selectively inhibit connexin channels. Antibodies, including nanobodies, against the connexin protein display strong selectivity toward certain connexin subtypes; by contrast, several compounds exist that have multiple targets in addition to connexin channels. These include glycyrrhetinic acid and its derivative carbenoxolone, long-chain alcohols like heptanol and octanol, halogenated general volatile anesthetics like halothane, fatty acids like arachidonic acid and oleic acid, fatty acid amides like oleamide and anandamide, fenamates (arylaminobenzoates) like flufenamic acid, niflumic acid and meclofenamic acid, 5-Nitro-2-(3-phenyl-propylamino)benzoic acid (NPPB), disodium 4,4'-diisothiocyanatostilbene-2,2'-disulfonate (DIDS), quinine, quinidine and quinine-derivatives like mefloquine, 2-aminoethoxydiphenyl borate (2-APB), polyamines like spermine and spermidine, and certain triphenylmethanes, triphenylethanes, triarylmethanes and cyclodextrins (reviewed in ref.[36]). Pannexin hemichannels are blocked by some of the non-specific connexin channel blockers such as carbenoxolone, NPPB and DIDS, by disodium 4-acetamido-4'-isothiocyanato-stilben-2,2'-disulfonate (SITS), indanyloxyacetic acid (IAA-94), probenecid and by $^{10}$Panx1 peptide.[37]

Considering all evidence available, there is an urgent need to improve preservation methods of grafts prior to implanting them into patients or animals.

BRIEF SUMMARY

This disclosure relates to the surprising finding that the combined block of gap junctions and hemichannels with connexin channel inhibitors (and, in some instances, combined with pannexin channel inhibitors) added to the solutions suitable to preserve grafts, strongly reduces cell death due to preservation methods such as cold storage/hypothermia, cryopreservation or vitrification, adjoined by the processes of thawing and/or washing of the grafts. An important notion here is that graft preservation allows exploiting the possibility of inhibiting both gap junctions and connexin hemichannels. In contrast, such global inhibition of connexin channels is impossible in the in vivo condition because gap junctions have an essential physiological role in tissue and organ function, coordinating the function of groups of cells. In other words, a condition that is generally considered as non-desirable for normal function and survival in vivo is, in this disclosure, described as desirable for survival in vitro.

DETAILED DESCRIPTION

Figure 1:
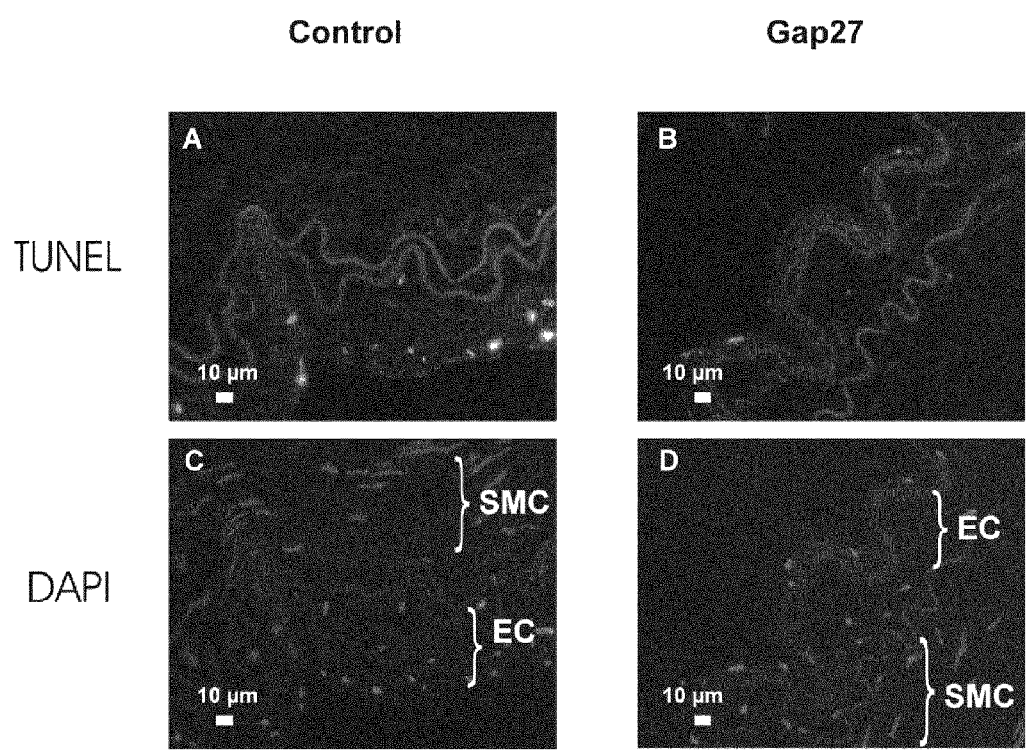
FIG. 1: Gap27 reduces apoptotic cell death in EC and SMC layers in cryopreserved human blood vessels.[38] Panels A-D. Example images of TUNEL (Panels A and B, green) and DAPI (Panels C and D, blue) stained sections of femoral arteries under control and after Gap27 treatment. The number of TUNEL-positive cells was visibly reduced by Gap27 in ECs and SMCs from intimal and medial layers, respectively.

Herein, it is disclosed that adding connexin channel inhibitors to solutions suitable to preserve grafts significantly reduces cell death due to particular preservation methods of the grafts. Such particular preservation methods encompass cold storage/hypothermia, cryopreservation or vitrification, followed by, or adjoined by, thawing and/or washing of the grafts. The latter methods can be damaging to particular cells within the grafts and may result in death of the cells.

Hence, this disclosure relates in first instance to the usage of connexin channel inhibitors to protect grafts against cell death due to preservation of the grafts prior to transplanting these grafts into human patients or animals. In a second instance, this procedure can be extended to include pannexin channel inhibitors to further potentiate the protective effect.

More in particular, this disclosure relates to the usage as described wherein the preservation includes cold storage, cryopreservation or vitrification, followed by thawing and/or washing of the grafts. In other words, this disclosure relates in particular (but not solely) to a method to protect grafts from injury and/or death via the usage of connexin channel inhibitors wherein injury/death is due to: 1) cold storage or hypothermia of the grafts, and/or 2) cryopreservation of the grafts, and/or 3) vitrification of the grafts, and/or 4) thawing of the grafts wherein thawing follows cryopreservation or vitrification, and/or 5) washing of the grafts wherein washing follows thawing.

With the term "grafts" is meant entire organs, composite tissues or a collection of cells isolated from animals or humans. Organ grafts include, for example, entire heart, uterus, kidney, liver, lung, trachea and parathyroid glands. Composite tissue grafts include, for example, fibrocartilage, bone, blood vessels, skin, cornea, nervous tissues, ovarian tissues and embryos. Cells or collections of cells include, for example, stem cells, hematopoietic cells, hepatocytes (liver cells) and non-fertilized or fertilized oocytes (zygotes).

With the terms "protecting grafts against cell death" is meant significantly reducing (i.e., $p \le 0.05$) the amount of death cells as measured by, for example, TUNEL staining to detect apoptotic cell death as described further or any other method known in the art such as nuclear staining to detect DNA fragmentation/condensation typical for apoptotic cells, caspase assays to detect apoptosis, annexin-based staining to detect early apoptosis, ethidium bromide or propidium iodide uptake assays or LDH release assays to detect membrane leakage in necrotic cells, within a graft after the graft is subjected to preservation methods and before the graft is administered or grafted or transplanted (the latter three terms can be used interchangeably) to a patient or animal.

The terms "protecting grafts against cell death" imply that the grafts will have a significantly better (i.e., $p \le 0.05$) biological functionality when compared to grafts that were not protected according to this disclosure. Hence, this disclosure further relates to the usage of connexin channel inhibitors, optionally including pannexin channel inhibitors, to improve the biological function of the grafts compared to grafts that were not protected according to this disclosure. With the term "biological functionality" is meant a measurable biological function of an organ, composite tissue or a collection of cells. For example, the inhibitors of this disclosure will significantly increase the capacity of hepatocytes to adhere to a substrate and secrete albumin, and will stimulate their Cyp3A4 activity when compared to the same capacities/activities of hepatocytes that were not protected according to this disclosure or will significantly increase the fertilization rate of oocytes when compared to the fertilization rate of oocytes that were not protected according to this disclosure.

The term "animal" refers to any animal and specifically relates to bovines, horses, ovines, cats, dogs and the like.

The term "cold storage" or "hypothermia" relates to well-known storing methods such as storing a graft at 4° C. or any other approach whereby the temperature is reduced to temperatures not below zero degrees Celsius. The term "cryopreservation" relates to storing a graft in any kind of instrument or method allowing reduction of the temperature below zero degrees Celsius. Typically, this involves the use of a −80° C. freezer or exposure or immersion in liquid nitrogen at −196° C. The term "vitrification" relates to an extremely rapid temperature reduction that results in a drastic increase of the water viscosity, thereby blocking the transition from the liquid to the crystalline state. The term "thawing" relates to any kind of instrument or method allowing the temperature to increase above zero degrees Celsius, thereby undoing the cryopreserved or vitrified state. The term "washing" relates to any well-known washing procedure of thawed grafts and specifically relates to progressively washing out a particular cryoprotectant, such as DMSO, glycerol or 1,2 propanediol by a stepwise reduction of the cryoprotectant concentration in the buffered solution wherein the grafts are preserved as is also described further.

The term "connexin channel inhibitor" relates to any compound, or a set of compounds, that is/are capable of inhibiting the biological activity of connexin proteins within both gap junctions and hemichannels. Hence, the term relates to a single compound inhibiting the biological activity of connexin proteins within both gap junctions and hemichannels or to a set of at least two compounds wherein one compound inhibits the biological activity of connexin proteins within gap junctions and wherein another compound inhibits the biological activity of connexin proteins within hemichannels. Hence, this disclosure further relates to the usage as described above wherein the connexin channel inhibitors are capable of inhibiting both gap junctions and hemichannels.

The term "connexin channel inhibitor" more specifically relates to substances that inhibit both gap junction channels and connexin hemichannels composed of a wide range of connexin protein isoforms. These substances include the peptides Gap26 and Gap27,[31, 39-41] antibodies directed against connexins, glycyrrhetinic acid and its derivative carbenoxolone, long-chain alcohols like heptanol and octanol, halogenated general volatile anesthetics like halothane, fatty acids like arachidonic acid and oleic acid, fatty acid amides like oleamide and anandamide, fenamates (arylaminobenzoates) like flufenamic acid, niflumic acid and meclofenamic acid, 5-Nitro-2-(3-phenyl-propylamino)benzoic acid (NPPB), disodium 4,4'-diisothiocyanatostilbene-2,2'-disulfonate (DIDS), quinine, quinidine and quinine-derivatives like mefloquine, 2-aminoethoxydiphenyl borate (2-APB), polyamines like spermine and spermidine, and certain triphenylmethanes, triphenylethanes, triarylmethanes and cyclodextrins.[36] Included in the definition of "connexin channel inhibitor" are any combination of these compounds listed above (e.g., carbenoxolone and Gap26, carbenoxolone and Gap27, or carbenoxolone, Gap26 and Gap27). The term "connexin channel inhibitor" also encompasses compounds with more selectivity, either toward the type of connexin channel, i.e., gap junctions or hemichannels, or toward the specific connexin subtype from which these channels are built, i.e., compounds that inhibit Cx43 channels but less so channels composed of other connexins. The term "connexin channel inhibitor" may thus, in some particular embodiments, include specific blockers of connexin hemichannels that do not inhibit gap junctions, called "specific connexin hemichannel inhibitors." Specific connexin hemichannel inhibitors are typically peptides that are identical to a sequence on the intracellular loop of the connexin protein, for example, Gap19 for hemichannels composed of Cx43[28] or Gap24 for Cx32 hemichannels.[42] In general, a "specific connexin hemichannel inhibitor" is peptide identical to an amino acid sequence on the intracellular loop of the connexin protein.

The term "pannexin channel inhibitor" defines blockers of channels composed of pannexins and includes the following chemical substances: [10]Panx1 peptide, carbenoxolone, probenecid, NPPB, DIDS, SITS and IAA-94. Because pannexin channel inhibitors essentially inhibit hemichannels, they are considered in this disclosure as a special group of the above-defined "connexin channel inhibitors" and are thus included in the definition of the connexin channel inhibitors.

Hence, this disclosure relates to the usage as described above wherein the connexin channel inhibitor is Gap26, Gap27 or any combination thereof, or, is Gap26 and/or Gap27 combined with any of the following substances: antibodies directed against connexins, glycyrrhetinic acid, carbenoxolone, heptanol, octanol, halothane, arachidonic acid, oleic acid, oleamide, anandamide, flufenamic acid, niflumic acid, meclofenamic acid, 5-Nitro-2-(3-phenyl-propylamino)benzoic acid (NPPB), disodium 4,4'-diisothiocyanatostilbene-2,2'-disulfonate (DIDS), quinine, quinidine, mefloquine, 2-aminoethoxydiphenyl borate (2-APB), spermine, spermidine, triphenylmethanes, triphenylethanes, triarylmethanes, cyclodextrins, the specific connexin hemichannel inhibitors Gap19 and/or Gap24, and the pannexin channel inhibitors [10]Panx1 peptide, probenecid, SITS and/or IAA-94.

This disclosure further specifically relates to the usage as described above wherein Gap27 is the connexin mimetic peptide having the consensus amino acid sequence $X_1X_2PTEKX_3X_4FX_5X_6$ (SEQ ID NO:1), wherein $X_1$ is S or A, $X_2$ is R or K, $X_3$ is T, N or K, $X_4$ is I, V or L $X_5$ is I, T, L or M and $X_6$ is I, V, L or Y, or a shortened version of SEQ ID NO:1, wherein the amino acids $X_4FX_5X_6$ or $FX_5X_6$ or $X_5X_6$ or $X_6$ are deleted, and/or wherein Gap26 is the connexin mimetic peptide having the consensus amino acid sequence $X_1CX_2DX_3X_4X_5PX_6SX_7X_8R$ (SEQ ID NO:3), wherein $X_1$ is V, A or I, $X_2$ is Y or F, $X_3$ is K, Q, A, E, H, R, N or D, $X_4$ is S, A, F or Y, $X_5$ is F or A, $X_6$ is I, V or L, $X_7$ is H, N or L and $X_8$ is V, I or R, and/or wherein Gap19 is the connexin mimetic peptide having the amino acid sequence KQIEIKKFK (SEQ ID NO:4), and/or wherein Gap24 is the connexin mimetic peptide having the amino acid sequence GHGDPLHLEEVKC (SEQ ID NO:5), and/or wherein the [10]Panx1 peptide is the pannexin mimetic peptide having the amino acid sequence WRQAAFVDSY (SEQ ID NO:6).

It should be clear that a skilled person could delete or add amino acids to the C and/or N-terminus of the connexin and/or pannexin mimetic peptides of this disclosure without having the effect that the peptides lose their inhibitory function. For example, it should be clear that to the N-terminus of SEQ ID NO:1 or to the N-terminus of the above-described shortened version of SEQ ID NO:1 (wherein 1 to 4 C-terminal amino acids are deleted), 1 or 2 additional amino acids can be added without having the effect that Gap27 or its truncated version loses its connexin channel-inhibitory function.

The connexin mimetic peptides Gap19 and Gap24 of this disclosure can be coupled to cell internalization sequences such as, not limited to, the HIV-derived TAT sequence YGRKKRRQRRR[43] (SEQ ID NO:7) or the Drosophila-derived antennapedia internalization sequence RQPKIWFPNRRKPWKK[44, 45] (SEQ ID NO:8).

Hence, this disclosure relates to the usages as described above wherein the connexin mimetic peptides Gap19, Gap24, or Gap19 and Gap24 are coupled to a cell internalization sequence. Several internalization sequences are well known in the art. More specifically, this disclosure relates to the usages as indicated above wherein internalization sequences are the TAT sequence YGRKKRRQRRR (SEQ ID NO:7) or the antennapedia internalization vector RQPKIWFPNRRKPWKK (SEQ ID NO:8). In other words, Gap19 or Gap24 can be coupled to the sequence YGRKKRRQRRR (SEQ ID NO:7) or the sequence RQPKIWFPNRRKPWKK (SEQ ID NO:8), which allows the mimetic peptides to more efficiently enter a target cell that has to be protected according to this disclosure.

This disclosure more specifically relates to the usage as described above wherein the sequence of Gap27 is the amino acid sequence SRPTEKTIFII (SEQ ID NO:2).

This disclosure further specifically relates to the usage as described above wherein the grafts are oocytes, hepatocytes, stem cells, vascular grafts, heart or uterus. Oocytes, hepatocytes, stem cells, heart or uterus are also described elsewhere in this application. A vascular graft is a piece of blood vessel, isolated from an animal or human person with the intention of being subsequently used for implantation into an animal or human to replace a damaged blood vessel or correct a blood vessel defect.

This disclosure more specifically relates to the usage as described above wherein the vascular graft are human arteries or veins, and even more specifically, wherein the arteries are aorta, femoral arteries, iliac arteries, tibial arteries or internal thoracic arteries, and wherein the veins are saphenous veins or iliac veins.

This disclosure further relates to an in vitro method to protect grafts against cell death due to preservation of the grafts comprising: a) obtaining a graft from a donor, b) adding a protective amount of connexin channel inhibitor to a solution suitable to preserve grafts, c) placing the graft into the solution containing the connexin channel inhibitor, and d) preserving the grafts embedded in the solution containing the connexin channel inhibitor.

The terms "obtaining a graft from a donor" relate to any well-known method in the art to harvest a graft or tissue from a living or deceased animal or human. The terms "adding a protective amount of connexin channel inhibitor to a solution" relates to adding specific amounts in the order of 5 to 500 µM of connexin channel inhibitors to a solution that will significantly reduce cell death within the graft when compared to the grafts preserved in solutions without the connexin channel inhibitors.

This disclosure more specifically relates to an in vitro method as described above wherein preservation includes cold storage/hypothermia, cryopreservation or vitrification, followed by thawing and washing the grafts.

More specifically, this disclosure relates to an in vitro method as described above wherein the connexin channel inhibitor is separately added to a solution suitable to wash previously cryopreserved and thawed grafts.

This disclosure further relates to an in vitro method as described above wherein the solution suitable to cryopreserve grafts comprises Hank's Buffered Salt Solution (HBSS), 4-(2-hydroxyethyl)-1-piperazineethanesulfonic acid buffer (HEPES buffer) and dimethylsulfoxide (DMSO) and wherein the solution suitable to wash previously cryopreserved and thawed grafts comprises HBSS and HEPES buffer. Other possible solutions suitable to cryopreserve grafts are glycerol, trehalose, dextran, ethylene glycol, polyethylene glycol, propylene glycol (1,2 propanediol), butylene glycol (2,3 butanediol), polyvinylpyrrolidone and chondroitin sulphate.

EXAMPLES

Example 1

Connexin Channel Inhibitors have Beneficial Effects on Blood Vessels after Cryopreservation/Thawing[38]

Materials and Methods
Tissue Preparation

Tissue samples of human femoral artery and saphenous vein were obtained from deceased donors (age: 45±1.7 years) according to a protocol that was approved by the ethical committee of the University Hospital Ghent, Belgium. Blood vessels were selected and procured using the Superior Health Council Belgium guidelines. Exclusion criteria were: presence of ulcers, calcific atheromas, rupture of intima or media, traction lesions due to prelevation in arteries; signs of phlebitis, atheromatosis, parietal abnormalities, or lesions of intima in veins. The vessels were placed in HBSS-HEPES and prior to cryopreservation, DMSO (15%) was added. DMSO is the most commonly used permeating cryoprotecting agent for cryopreservation of blood vessels[46] and concentrations up to 15% were shown to not damage the vessels.[47] In Gap27-treated vessels, the peptide was added to the HBSS-HEPES-DMSO solution at a final concentration of 200 µM. Grafts were cryopreserved at 1° C./minute in a −80° C. freezer and, after two weeks, stored for at least another two weeks in a liquid nitrogen container (−196° C.).

For vessel analysis and cell death studies, tissues were thawed in a 37° C. water bath and kept on ice before the next steps. DMSO was then progressively washed out by a stepwise reduction of the DMSO concentration in the HBSS-HEPES solution. To that purpose, the blood vessels remained for 4 minutes in HBSS-HEPES solution with, respectively, 10%, 5%, 2.5% and 0% DMSO. In Gap27-treated vessels, the peptide (200 µM) was present during DMSO washout.

Experiments were performed to verify the effect of Gap27 when included during cryopreservation/thawing only or during DMSO washout only.

After DMSO washout, vessels were embedded in paraffin. To this purpose, blood vessels were transferred to a neutral buffered 4% formalin solution for fixation during 24 hours and were then embedded in paraffin. Paraffin-embedded vessel specimens were cut into 5 µM serial sections along a transverse plane and were then stained with hematoxylin and eosin for general inspection, immunostained for connexins to establish the expression of various connexin types in the blood vessels or stained for cell death (apoptosis) making use of in situ terminal TdT-mediated dUTP nick end-labeling (TUNEL) with the In Situ Cell Death Detection Kit (Roche, Vilvoorde, Belgium). After any of these staining procedures, images were taken on a Nikon TE300 inverted microscope using a ×10 or ×20 objective and equipped with a Nikon DS-Ri1 cooled color CCD camera (Nikon Belux, Brussels, Belgium).

Immunostaining

Paraffin slices were deparaffinized and subsequently incubated with an antigen retrieval solution (Vector, Lab Consult, Brussels, Belgium). Preincubation with a blocking buffer (Bovine serum albumin, 5 mg/ml; bovine skin gelatin, 0.1%; TRITON® X-100, 0.25% in phosphate-buffered saline (PBS)) was done for 30 minutes at room temperature. Sections were incubated overnight at 4° C. with primary antibody (anti-Cx43 polyclonal AB (1/250, Sigma, Belgium), anti-Cx37 polyclonal (1/100, Zymed, Life Technologies) or anti-Cx40 polyclonal (1/10, Thermo Fisher, Belgium) diluted in blocking solution. After washing, a secondary antibody conjugated to Alexa-594 (1/500, Molecular Probes, Life Technologies) was added. The sections were mounted with an antifade solution containing 4',6-diamidino-2-phenylindole (DAPI) (Vectashield, Lab Consult) for nuclear staining. Images were acquired on a Nikon TE300 inverted epifluorescence microscope with a ×20 objective and camera as referred to before.

Apoptosis Assay

Embedded artery or vein sections were deparaffinized, rehydrated through graded alcohol, and permeabilized with 0.1% TRITON® X-100 at room temperature (8 minutes incubation). Slides were rinsed twice in a phosphate-buffered saline (PBS). Apoptosis was detected through in situ terminal deoxynucleotidyl transferase (TdT)-mediated deoxyuridine triphosphate (dUTP) nick end-labeling (TUNEL), using the In Situ Cell Death Detection Kit (Roche, Vilvoorde, Belgium). Slides were incubated with the TUNEL reaction mixture containing TdT and fluorescein-dUTP for 1 hour at 37° C.; thereafter, they were rinsed three times in PBS and mounted as described for immunostaining. Control experiments performed on C6 glioma cells stably transfected with Cx43 exposed to staurosporine (2 µM, 6 hours) induced massive TUNEL positivity while exposure to the DMSO vehicle had no effect. TUNEL-stained blood vessel tissue sections were examined by epifluorescence microscopy as described for immunostaining. Four areas from each slide were examined and five slides per blood vessel were analyzed. The number of TUNEL-positive cells is given as a percentage of the total number of cells quantified from DAPI-positive counts.

Pharmacological Agents

Gap27 (SRPTEKTIFII (SEQ ID NO:2)) and scrambled Gap27 (TFEPIRISITK (SEQ ID NO: )) were synthesized by Thermo Fisher Scientific (Ulm, Germany) at >80% purity. HBSS-HEPES (Gibco, Merelbeke, Belgium) contained (in mM) $CaCl_2$, 1.26; $MgCl_2\text{-}6H_2O$, 0.493; $MgSO_4\text{-}7H_2O$, 0.407; KCl, 5.33; $KH_2PO_4$, 0.441; $NaHCO_3$, 4.17; NaCl, 137.93; $Na_2HPO_4$, 0.338; D-Glucose (Dextrose), 5.56; Phenol Red, 0.0266. PBS contained (in mM) NaCl, 137; KCl, 2.68; $KH_2PO_4$, 1.47; $Na_2HPO_4.2H_2O$, 6.46; pH 7.4. Staurosporine was obtained from Sigma (Bornem, Belgium).

Statistical Analysis

All data are expressed as mean±SEM. Statistical analysis between groups was performed using Friedman Test with Dunn's post-t-test. Proportions were compared using Pearson's Chi-square test. Differences in cell death between control conditions of both blood vessels are analyzed by unpaired Student's t-test. Correlations were assessed by Pearson's Correlation tests. A value of $P<0.05$ was considered as statistically significant. The symbol n represents the number of blood vessels.

Results
Connexin Expression in Human Femoral Arteries and Saphenous Veins

Immunostainings demonstrated the presence of the major vascular connexins, Cx37, Cx40 and Cx43 in the intimal and medial layers of human cryopreserved blood vessels. Cx37 was mainly found in the intimal EC layer of saphenous veins, while it was present in intimal EC and medial SMC layers in femoral arteries. Cx40 was found in both arteries and veins and was present in the intimal and medial layers. Cx43 was most abundantly present and was mainly located in the medial layer of femoral arteries and in intimal and medial layers of saphenous veins.

Gap27 Reduces Apoptotic Cell Death in Cryopreserved Human Blood Vessels

Figure 2:
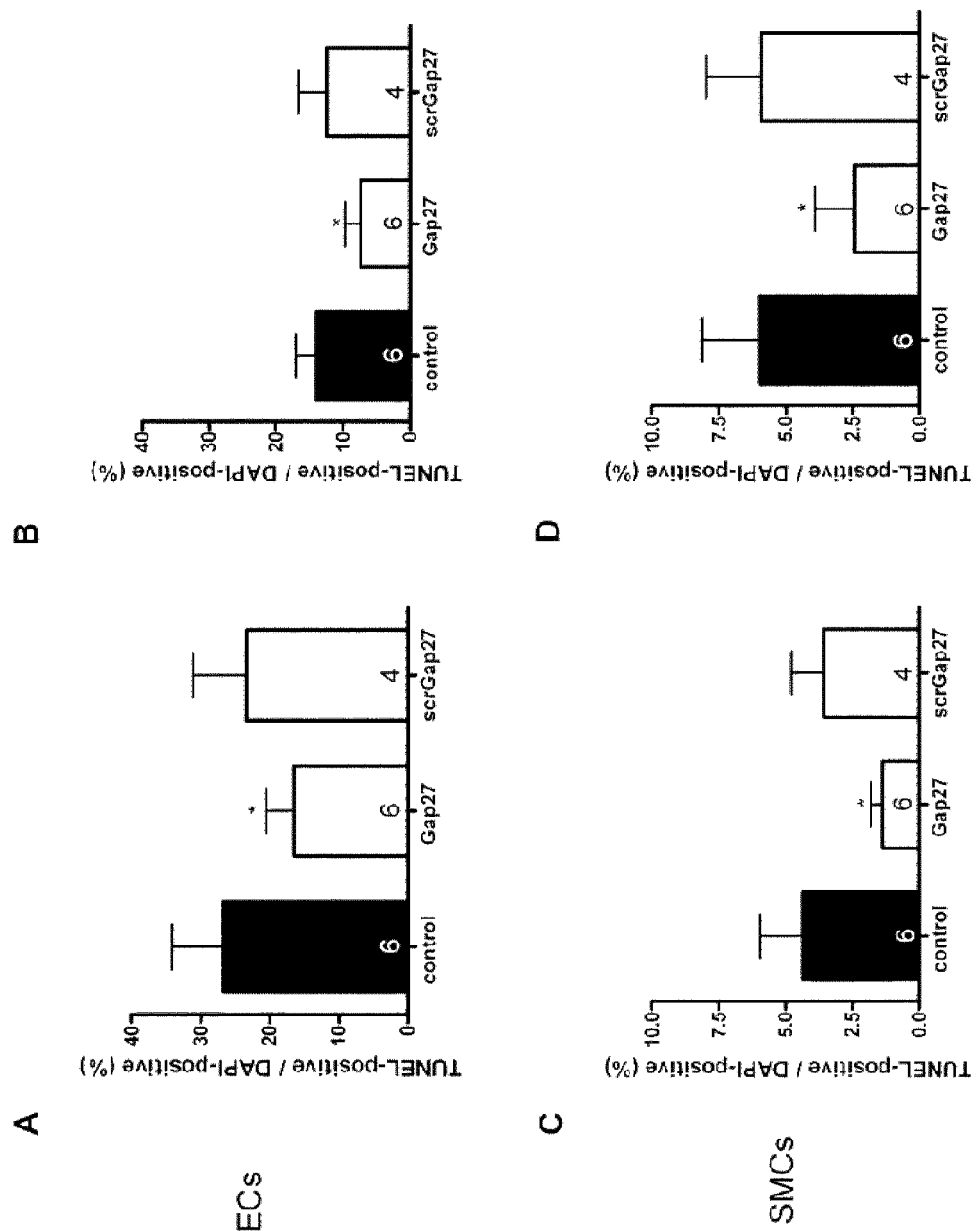
FIG. 2: Gap27 reduces apoptotic cell death in cryopreserved human blood vessels—average data.[38] Apoptotic cell death in ECs (Panels A, B) and SMCs (Panels C, D) of femoral arteries (Panels A, C) and saphenous veins (Panels B, D). The number of TUNEL-positive cells was significantly reduced by Gap27 in ECs and SMCs. Gap27 with a scrambled peptide sequence had no significant effects on cell death counts. The numbers of vessels are indicated in the bars. * $P<0.05$

In order to quantify cell death in cryopreserved/thawed blood vessels, TUNEL stainings were performed to detect apoptotic cell death. As can be appreciated from FIG. 1, Panels A and C, non-treated blood vessels displayed clearly discernable TUNEL positivity in the intimal and medial layers. As verified, no significant correlation was found when the degree of TUNEL positivity varied with the duration of the time interval between vessel procurement and start of cryopreservation. Interestingly, it was found that Gap27 (200 µM) visibly reduced TUNEL positivity counts when it was present during cryopreservation, thawing and DMSO washout. Average data of several such experiments are given in FIG. 2. In femoral arteries, ~27% of the ECs and ~5% of the SMCs were TUNEL-positive under control conditions. Gap27 significantly reduced these cell death counts by more than ⅓ in the intimal layer and by more than ⅔ in the medial layer. In saphenous veins, TUNEL positivity was ~14% in ECs and ~6% in SMCs. Gap27 significantly reduced these counts by almost ½ in ECs and by more than ½ in SMCs. Gap27 with a scrambled peptide sequence had no significant effects on cell death counts. Thus, Gap27 more than halved cell death in SMCs while cell death reduction was less than half in ECs.

Cell death in control (without Gap27) was much more prominent in ECs than in SMCs (ECs: 27 and 14% in arteries and veins respectively vs. SMCs: 5 and 6%) and, as a consequence, the fraction of cells rescued by Gap27 may be more important in ECs as compared to SMCs. Therefore, the protective effect of Gap27 relative to the total number of cells (EC or SMC) was calculated as an alternative to calculations relative to the number of dead cells. Table 1 summarizes these two measures of Gap27 protection and demonstrates that the cell mass rescued by Gap27 was larger in ECs than in SMCs.

TABLE 1

Protective effect of Gap27 on cell death in ECs and SMCs.

|  | Protection relative to total number of dead cells (%) | | Protection relative to total number of cells (%) | |
| --- | --- | --- | --- | --- |
|  | Arteries | Veins | Arteries | Veins |
| EC | 32 ± 8 (n = 11) | 51 ± 8 (n = 13) | 11 ± 4 (n = 11) | 12 ± 4 (n = 13) |
| SMC | 73 ± 7 (n = 11) | 71 ± 6 (n = 13) | 6 ± 3 (n = 11) | 6 ± 2 (n = 13) |

Average values express inhibitory effect based on Gap27 treatment data

In a next step, it was determined in which phase Gap27 exerted most of its protective effects: during cryopreservation/thawing or during DMSO washout. Thus, cell death with Gap27 being included either during cryopreservation/thawing or during DMSO washout was investigated. It was found that inclusion of Gap27 during DMSO washout only, slightly (but non-significantly) reduced cell death in ECs and SMCs, while inclusion during cryopreservation/thawing only, always gave larger and statistically significant protective effects in both femoral artery and saphenous vein.

Example 2

Connexin Channel Inhibitors have Beneficial Effects on Cumulus-Oocyte Complexes after Vitrification/Thawing Oocytes are surrounded by cumulus cells that prominently express Cx43 forming gap junctions as well as hemichannels.[48-50] Gap junctions composed of Cx37 exist between cumulus cells and oocytes[51, 52] and often the cumulus-oocyte complex persists even after enzymatic treatment. Tests were performed as to whether connexin channel inhibitors have beneficial effects on the cell viability of the oocyte-cumulus complex after vitrification/thawing in a bovine model system. Fertilization and development were also looked at, and furthermore tested whether connexin channel inhibitors were beneficial during a simulated transportation phase after vitrification/thawing. The main findings are that connexin channel inhibitors slightly improve the (already high) viability of the cumulus cells but strongly increase the fertilization rate (approximate seven-fold increase). Inclusion of connexin channel inhibitors during simulated transportation indicated that this inclusion rescues up 3.1%-8.7% of the total cumulus cell mass from dying.

Materials and Methods

Isolation, Vitrification and Thawing of Bovine Cumulus-Oocyte Complexes (COCs)

All procedures used were in accordance with the guidance principals for care and use of laboratory animals of the Laboratory Animal Ethical Commission of Ghent University. Bovine cumulus-oocyte complexes (COCs) were aspirated from ovaries collected at a local slaughterhouse. Immature COCs were recovered from the follicular fluid, washed two times in HEPES-TALP (see below under the heading "Pharmacological agents and solutions" of Materials and Methods), and matured for 22 hours in groups of 60 in 500 mL of modified bicarbonate-buffered TCM199 (Gibco BRL, Life Technologies) supplemented with 20% heat-inactivated fetal calf serum (FCS; Sigma-Aldrich) at 38.5° C. in a humidified 5% $CO_2$ incubator. Vitrification was performed in two steps: an equilibration (EQ) and a vitrification step (VS). Equilibration solution was composed of M199/Hanks/HEPES supplemented with 20% fetal calf serum (FCS)+7.5% ethylene glycol+7.5% DMSO. The vitrification solution contained: M199/Hanks/HEPES supplemented with 20% FCS+15% ethylene glycol, 15% DMSO and 0.5 M sucrose. The COCs were washed by transferring them sequentially in three drops of 100 µl EQ solution (3 minutes residence in the first two drops and 6 minutes in the last drop) and then placed stepwise in five 100 µl drops VS solution (5 seconds in each drop except for the fifth that lasted 10 seconds). The connexin channel inhibitor Gap27 was added to the fifth drop of VS solution at a final concentration of 200 µM (the Gap27 sequence is given below under the heading "Pharmacological agents and solutions" of Materials and Methods). The control condition consisted of a drop solution without any added Gap27. COCs were placed in a manufactured cryotop and transferred immediately to liquid nitrogen (−196° C.).

After 24 hours' storage in liquid nitrogen, the COCs were thawed by transferring them to a warming solution at 37° C. composed of M199/Hanks/HEPES+20% FCS+1.25 M sucrose for 1 minute. This was followed by a three-step wash-out of the hyperosmolar sucrose (reduced from 1.25 M to 0.62, 0.31 and 0 M, respectively; duration of each wash was 3 minutes, 5 minutes and 5 minutes, respectively). In the Gap27 treatment condition, the peptide concentration was gradually diluted over these three washing steps, halving its concentration with each transfer step (reduced from 200 µM in cryopreservation solution to 100, 50 and 0 µM, respectively). In the text that follows, "thawing" denotes the combination of warming and wash out of the hyperosmolarity.

Cell Death Assay

COCs were fixed in neutral buffered 4% formalin solution after thawing. Fixed COCs were permeabilized with 0.1% TRITON® X-100 at room temperature (8-minute incubation). COCs were rinsed twice in a phosphate-buffered saline (PBS, see Pharmacological agents and solutions). Cell death was detected by in situ terminal deoxynucleotidyl transferase (TdT)-mediated deoxyuridine triphosphate (dUTP) nick end-labeling (TUNEL), using a commercial In Situ Cell Death Detection Kit (Roche, Vilvoorde, Belgium). COCs were incubated with the TUNEL reaction mixture containing TdT and fluorescein-dUTP for 1 hour at 37° C.; thereafter, they were rinsed three times in PBS and mounted with an antifade solution containing 4',6-diamidino-2-phenylindole (DAPI) (Vectashield, Lab Consult) for nuclear staining. Slides were examined by epifluorescence microscopy using a Nikon TE300 inverted microscope with a ×10 objective and equipped with a Nikon DS-Ri1 cooled color CCD camera (Nikon Belux, Brussels, Belgium).

Insemination of Bovine Oocytes

Frozen-thawed bovine sperm was separated over a Percoll gradient (45% and 90%; Pharmacia, GE Healthcare), washed, and diluted in Fert-TALP (composition see below under "Pharmacological agents and solutions") to a final sperm concentration of $1 \times 10^6$ spermatozoa/mL. The matured COCs were washed in 500 mL Fert-TALP and incubated with sperm. After 20 hours of co-incubation, the presumed zygotes were vortexed to remove excess sperm and cumulus cells.

Fertilization Rate and Cleavage Rate

For fertilization rate, zygotes were transferred to a neutral buffered 4% formalin solution for fixation during 2 hours and were then stained with Hoechst dye to identify fertilized cells that contained two pronuclei.

To determine the cleavage rate, zygotes were washed and placed in groups of 30 in 50 mL droplets of synthetic oviduct fluid (composition see below under "Pharmacological agents and solutions") supplemented with 5% FCS and cultured at 38.5° C. in 5% $CO_2$, 5% $O_2$, and 90% $N_2$; cleavage rate was determined after 48 hours in culture.

Simulated Transportation Conditions

A transportation phase of the COCs was simulated after the vitrification/thawing procedure by storing control vitrified COCs (without Gap27) in HEPES-TALP for 5 hours at 37° C. This was performed with or without Gap27 peptide (200 µM) present in the transportation phase medium. Afterward, cell death was evaluated via TUNEL assays as described before.

Pharmacological Agents and Solutions

The connexin channel inhibitor Gap27 (SRPTEKTIFII (SEQ ID NO:2)) was synthesized by Pepnome Limited (Jida Zhuhai, China) at >80% purity.

Hepes-TALP contained (in mM): 114 NaCl, 3.1 KCl, 0.3 $NaH_2PO_4$, 2.1 $CaCl_2$, 0.4 $MgCl_2$, 2 $NaHCO_3$, 0.2 sodium pyruvate, 10 sodium lactate, 10 µg/ml gentamycin sulphate, 10 Hepes and 3 mg/ml bovine serum albumin (BSA). Phosphate-buffered saline (PBS) contained (in mM): 137 NaCl, 2.68 KCl, 0.90 $CaCl2$, 0.334 $MgCl_2.6H_2O$, 1.47 $KH_2PO_4$, 6.46 $Na_2HPO_4.2H_2O$ (pH 7.4).

Fert-TALP consisted of HEPES-TALP solution, supplemented with 6 mg/ml BSA and 4 mM $NaHCO_3$.

Synthetic oviduct fluid (SOF) contained Eagle's basal medium (BME, 50×, 1/50 dilution), minimum essential medium Eagle (MEM 100×, 1/100 diluted) and supplemented with (in mM): 2.8 myo-inositol, 0.3 sodium citrate, 107.6 NaCl, 7.2 KCl, 1.2 $KH_2PO_4$, 1.5 $MgSO_4$ 5 $H_2O$, 7.1 Na Lactate, 28.4 $NaHCO_3$, 0.7 Na pyruvate, 1.8 $CaCl_2.2H_2O$, 0.4 glutamine, 50 µg/ml gentamycine, 0.4% BSA, 5 µg/ml insulin, 5 µg/ml transferrin, 5 ng/ml selenium.

Statistical Analysis

All data are expressed as mean±SEM. Statistically significant differences are evaluated using unpaired Student's t-test. A value of P<0.05 was considered as statistically significant. The symbol n represents the number of oocytes.

Results

Effect of Gap27 Treatment During Vitrification/Thawing on COC Viability

Inclusion of Gap27 during vitrification/thawing reduced the cell death (TUNEL assay) of cumulus cells in vitrified/thawed COCs from 4.11% (±0.95, n=25) to 1.68% (±0.67, n=16). This corresponds to a ~59% reduction when expressed relative to the total number of dead cells in control. In terms of the cell mass that can be rescued by Gap27, the effect was limited and corresponded to ~2.4% (effect size relative to the total number of cells). No cell death of the oocytes after vitrification/thawing, whatever the treatment, was observed in any of the experiments.

Effect of Gap27 Treatment During Vitrification/Thawing on the Fertilization and Cleavage Rate The fertilization rate in control non-vitrified COCs was 81% (n=26). Control vitrified/thawed COCs had a fertilization rate of 6% (n=16), while the fertilization rate prominently increased to 41.2% (n=17) for COCs that were vitrified/thawed in the presence of Gap27.

The cleavage rate was 96% (n=25) in control non-vitrified COCs and amounted to 28% (n=25) in control vitrified/thawed COCs as well as in Gap27-treated COCs.

Effect of Gap27 Treatment During Simulated Transportation on COC Viability

Testing was performed as to whether Gap27 could improve COC viability upon inclusion in the media during a simulated transportation phase (5 hours total duration, see Materials and Methods) applied after the vitrification/thawing procedure. In these experiments, vitrification/thawing were done under control conditions and Gap27 was only present in the transportation medium.

Gap27 reduced cell death of cumulus cells when the COCs were exposed to the simulated transportation condition at 37° C. from 20.3% (±11.0, n=5) to 13.8% (±5.17, n=6). This corresponds to a ~32% reduction of the mass of dead cells and a Gap27 rescue effect of ~6.5% relative to the total mass of cells. In this set of experiments, the cloud of cumulus cells (thickness ~100 µm) was left intact without attempting to reduce its size. In a next set of experiments, the cumulus cell layer was reduced to 1-5 cell layers. In this case, Gap27 reduced cell death from 16.2% (±5.39, n=9) to 7.54% (±2.49, n=5), which corresponds to a ~54% reduction of the dead cell mass and a Gap27 rescue effect of ~8.7% of the total cell mass.

These experiments were repeated (intact COCs) with simulated transportation at 0° C. Here, Gap27 reduced cell death from 5.96 (±1.49, n=15) to 2.82% (±0.07, n=14). This corresponds to a ~53% reduction of the dead cell mass and a Gap27 rescue effect of ~3.1% of the total cell mass.

Example 3

Connexin Channel Inhibitors Improve the Functional State of Hepatocytes after Cryopreservation/Thawing Examples 1 and 2 demonstrated beneficial effects of connexin channel inhibitors on the outcome of moderately complex tissues consisting of two different cell types (endothelial cell/smooth muscle cells and cumulus cells/oocyte, respectively) after cryopreservation or vitrification followed by thawing. This example reports on data obtained in a single cell type, the hepatocyte, isolated in suspension from the murine liver and exposed to cryopreservation/thawing.

Cryopreserved hepatocytes are clinically relevant since these cells serve as a model for human livers and can be used for investigations on drug metabolism and toxicity. Human hepatocytes offer interesting perspectives for cell-therapeutic approaches to liver disease, for example, for the treatment of acute liver failure and in the context of certain metabolic disorders. Hepatocytes abundantly express Cx26 and Cx32. Additionally, upon isolating hepatocytes, Cx43 is significantly up-regulated[53] and preliminary evidence indicates that this is also the case for Panx1. Testing was performed to determine whether connexin channel inhibitors, pannexin channel inhibitors and a combination of both had beneficial effects on hepatocyte viability and function (adhesion, albumin secretion and Cyp3A4 activity) after cryopreservation/thawing. Experiments were included that tested whether connexin/pannexin channel inhibitors were beneficial during a simulated transportation phase after cryopreservation/thawing.

The most salient findings are that connexin/pannexin channel inhibition during cryopreservation/thawing substantially improves hepatocyte adhesion in subsequent culture (⅔ more cells) and promotes hepatocyte function (Cyp3A4 activity and albumin secretion). Inclusion of connexin/pannexin channel inhibitors during simulated transportation rescued ~5.4% of the total cell mass from dying.

Materials and Methods

Isolation, Cryopreservation and Thawing of Murine Hepatocytes

Primary hepatocytes were isolated from adult mouse liver (8-14 weeks of age) using a two-step collagenase perfusion method as described by Conçalves et al.[54] Cells were immediately transferred to cryovials, suspended in 1 mL cryopreservation medium at a density of 3.2 million cells/mL. Cryovials were then placed in an isopropanol box in a −80° C. freezer for 4 hours and then transferred to a liquid nitrogen container (−196° C.) for storage over at least 24 hours. Cryopreservation medium consisted of William's E medium (Life Technologies), supplemented with 10% FBS (Life Technologies), 10% DMSO (Sigma) and with or without the connexin and/or pannexin channel inhibitors. The connexin channel inhibitors used were [43]Gap27 and [32]Gap27, and [10]Panx1 as a pannexin channel inhibitor, each at a concentration of 150 µM (peptide sequences see below under the heading "Pharmacological agents and solutions" of Materials and Methods).

Cryovials were thawed in a 37° C. water bath and the hepatocytes were immediately washed in complex William's E medium (Life Technologies), supplemented with L-glutamine (292 mg/mL) (Invitrogen), glucagon (7 ng/mL) (Sigma), insulin (0.5 µg/mL) (Sigma), hydrocortisone (25 µg/mL), EGF (10 ng/mL), 10% v/v FBS (Life Technologies), 50 U/mL penicillin (Life Technologies) and 50 µg/mL streptomycin (Life Technologies).

Cell Death Assay

After thawing, hepatocytes were immediately fixed in 4% neutral buffered formalin solution for 20 minutes. Cells were then permeabilized with 0.1% TRITON® X-100 at room temperature (8 minutes incubation). Hepatocytes were rinsed twice in a phosphate-buffered saline (PBS). Cell death was detected by in situ terminal deoxynucleotidyl transferase (TdT)-mediated deoxyuridine triphosphate (dUTP) nick end-labeling (TUNEL), using the In Situ Cell Death Detection Kit (Roche, Vilvoorde, Belgium). Hepatocytes were incubated with the TUNEL reaction mixture containing TdT and fluorescein-dUTP for 1 hour at 37° C.; thereafter, they were rinsed three times in PBS and mounted with an antifade solution containing 4',6-diamidino-2-phenylindole (DAPI) (Vectashield, Lab Consult) for nuclear staining. Slides were examined by epifluorescence microscopy. Images were acquired on a BD pathway 435 bioimaging station using a ×10 objective.

Cell Adhesion

Thawed hepatocytes were grown on well plates coated with 0.1% rat tail collagen type I (BD Biosciences) in William's E medium (Life Technologies) with supplementation as used after thawing. Cell adhesion was evaluated at different time points by counting Hoechst-positive cells and expressing them relative to the total cell count (adhering cells and those present in the culture medium).

Cytochrome Assay

Cyp3A4 activity of the hepatocytes was analyzed using a P450-Glo™-CYP3A assay (Promega) according to the manufacturer's protocol for cell-based assays. The hepatocytes were cultured for 1 hour in media containing luciferin-IPA (1:1000). After 1 hour, an equal volume of the liquid was transferred to a 96-well plate and incubated with an equal volume of detection reagent. After 20 minutes, luciferase activity was detected using a Wallac 1420 Victor³™ multi-label counter (PerkinElmer). The detected luminescence was normalized for the total amount of cells present (Hoechst-positive cell counts). In all experiments, background signal in the absence of cells was subtracted.

Albumin Secretion

Albumin secretion was determined from collected media samples. Albumin secretion was determined from collected media samples using a mouse albumin ELISA quantitation kit (Bethyl Laboratories, Inc., UK). Results were corrected for cross-reactivity with bovine albumin and normalized for the total cell counts.

Simulated Transportation Conditions

In order to investigate the effect of treatment with connexin/pannexin channel inhibitors during a transportation phase after cryopreservation/thawing, control cryopreserved hepatocytes (without connexin/pannexin channel inhibitors) were transferred to complex William's E medium for 5 hours at 0° C. or 37° C. In this medium, [43]Gap27, [32]Gap27 and [10]Panx1 were present or absent (control) and the effect on cell viability was evaluated via TUNEL assays as described before.

Pharmacological Agents and Solutions

[43]Gap27 (SRPTEKTIFII (SEQ ID NO:2)), [32]Gap27 (SRPTEKTVFT (SEQ ID NO:9)) and [10]Panx1 (WRQAAF-VDSY (SEQ ID NO:6)) were synthesized by Pepnome Limited (Jida Zhuhai, China) at >80% purity.

Phosphate-buffered saline (PBS) contained (in mM): 137 NaCl, 2.68 KCl, 0.90 CaCl2, 0.334 $MgCl_2.6H_2O$, 1.47 $KH_2PO_4$, and 6.46 $Na_2HPO_4.2H_2O$ (pH 7.4).

Statistical Analysis

All data are expressed as mean±SEM. Statistical significance was evaluated using a paired Student's t-test. A value of P<0.05 was considered as statistically significant. The symbol n represents the number of cell cultures.

Results

Effect of Connexin/Pannexin Channel Inhibition During Cryopreservation/Thawing on Hepatocyte Viability Including the connexin channel inhibiting peptides $^{43}$Gap27 and $^{32}$Gap27 during cryopreservation/thawing of hepatocytes reduced cell death from 8.55% (control) to 3.03% (data from one isolation experiment). This corresponds to ~65% reduction of the dead cell mass and a rescue effect of ~5.5% when expressed relative to the total cell mass. Inclusion of connexin channel inhibitors targeting Cx26 in the described experiments strengthens the latter effects.

Combined Connexin/Pannexin Channel Inhibition During Cryopreservation/Thawing of Hepatocytes Improves Cell Adhesion after Thawing Testing was performed to determine whether inclusion of $^{43}$Gap27, $^{32}$Gap27 and $^{10}$Panx1 during cryopreservation/thawing had any effects on the adhesion potential of the thawed hepatocytes during a period of subsequent culture. Hepatocytes showed improved adhesion when the three-peptide cocktail was present during the preceding cryopreservation/thawing phase (peptide cocktail not present during adhesion experiment). After 4 hours culture, adherent hepatocyte counts increased from 0.55 cells/mm$^2$ in control to 0.92 cells/mm$^2$ when the peptide cocktail was present during cryopreservation/thawing (n=2). After 24 hours, cell counts were 0.62 cells/mm$^2$ in control and 0.81 cells/mm$^2$ in the group treated with peptide cocktail during cryopreservation/thawing. This corresponds to a ~67% improvement of cell adhesion at 4 hours; after 24 hours, improvement is less (~31%) most probably because of compensatory cell growth in the non-treated group during prolonged culturing.

Combined Connexin/Pannexin Channel Inhibition During Cryopreservation/Thawing of Hepatocytes Increases Cyp3A4 Activity and Albumin Secretion Testing was performed to determine whether inclusion of $^{43}$Gap27, $^{32}$Gap27 and $^{10}$Panx1 during cryopreservation/thawing influenced the functional profile of the hepatocytes afterward. Table 2 summarizes Cyp3A4-reporter activities measured in one experiment. Cyp3A4 activity was increased in the peptide group compared (peptide washed out after thawing) to the control group and this was apparent over the different time points.

TABLE 2

Cyp3A4 activity in hepatocytes after cryopreservation/thawing without treatment (control) and in the group treated with peptide cocktail (peptide). Data expressed in arbitrary units (A.U.). The last column summarizes the improvement as a fold change.

|  | Control (A.U.) | Peptide (A.U.) | Fold increase |
| --- | --- | --- | --- |
| 24 hours | 406 | 643 | 1.58 |
| 48 hours | 563 | 700 | 1.24 |
| 72 hours | 540 | 701 | 1.30 |

In a similar experimental approach, the albumin secretion was determined as a function of time (Table 3). Albumin secretion was higher in the group that received peptide treatment during the preceding cryopreservation/thawing.

TABLE 3

Albumin secretion in hepatocytes after cryopreservation/thawing without treatment (control) and in the group treated with peptide cocktail (peptide). Data expressed in ng/ml. The last column summarizes the improvement as a fold change.

|  | Control (ng/ml) | Peptide (ng/ml) | Fold increase |
| --- | --- | --- | --- |
| 24 hours | 103 | 113 | 1.10 |
| 48 hours | 16.3 | 22.5 | 1.38 |
| 72 hours | 13.8 | 24.7 | 1.79 |

Combined Connexin/Pannexin Channel Inhibition During Simulated Transportation Substantially Improves Hepatocyte Viability Testing was performed to determine whether treatment with the $^{43}$Gap27, $^{32}$Gap27 and $^{10}$Panx1 cocktail could reduce hepatocyte cell death when the cells were exposed to a simulated transportation phase (5 hours total duration, see Materials and Methods) after cryopreservation/thawing. Here, cryopreservation/thawing were done under control conditions (without any peptide inclusion) and the peptide cocktail was only added to the transportation medium.

Performing simulated transportation at 37° C. was associated with high hepatocyte mortality (~43% cell death) and inclusion of the peptide cocktail did not make an apparent difference. When simulated transportation was done at 0° C., hepatocyte cell death decreased from 6.15% (control) to 0.72% (n=2, triplicate measurements) when $^{43}$Gap27/$^{32}$Gap27/$^{10}$Panx1 was present in the transportation medium. This corresponds to an ~88% reduction of the dead cell mass and a rescue effect of ~5.4% when expressed relative to the total cell mass.

Example 4

Connexin/Pannexin Channel Inhibition During Cryopreservation of Pluripotent Stem Cells Pluripotent stem cells, which include embryonic stem (ES) cells and induced pluripotent stem (iPS) cells, possess the ability to proliferate indefinitely without commitment in vitro and also have the potential to differentiate into all cell lineages belonging to the three embryonic germ layers. ES cells are derived from the inner cell mass of the preimplantation blastocyst, whereas iPS cells are generated from many different types of somatic cells by overexpression of only a few pluripotency-related transcription factors.[55]

Cryopreservation is a critical step in the storage and transportation of human ES cells and iPS cells. Efficient cryopreservation methods must offer high thawing efficiencies and maintain the pluripotency and differentiation potential of the cells. Pluripotent stem cells are one of the most interesting cell types for tissue engineering, cell therapy, basic scientific research, and drug screening. Fast advancement in these areas requires the availability of large amounts of safe and well-characterized pluripotent stem cells from stem cell banks. Therefore, optimized freezing protocols allowing the cryopreservation of large amounts of ES cells or iPS cells need to be established. Pluripotent stem cells usually grow as colonies of highly associated adherent cells, which require gap junctions and adhesion to extracellular matrix-coated surface. Human pluripotent stem cells are sensitive to traditional cryopreservation and thawing methods, in large part related to the disruption of this multicellular organization. In addition to necrosis caused by ice formation and osmotic shock, several other cryopreservation-induced events that affect the pluripotent stem cell survival include activated apoptosis, disruption of cell-cell and cell-matrix adhesions, and elevated ROS production.[56] The cryopreservation and vitrification approaches used for storing human pluripotent stem cells result in low survival rates after thawing, in the order of 5%-20% for cryopreservation and 25%-75% for vitrification. Additionally, many of the cells that do survive, appear to differentiate upon thawing and expansion.[57,58]

Human ES cells express Cx40, Cx43 and Cx45 at protein level[55, 59] and transcripts encoding almost all of the known connexin isoforms are found in hESCs[60] (Cx25, Cx26, Cx30, Cx30.2, Cx30.3, Cx31, Cx31.1, Cx31.9, Cx32, Cx36, Cx37, Cx40, Cx43, Cx45, Cx46, Cx47, Cx59 and Cx62). For Panx1, the scarce evidence available at present is at the mRNA level.[61] The data for iPS derived from human embryonic fibroblasts are similar to those in ECSs: Cx40, Cx43 and Cx45 at protein level and the same list as given above (except Cx32 and Cx36) at messenger level.[62]

A typical experiment is to test whether inclusion of connexin channel inhibitors or pannexin channel inhibitors in the media used for cryopreserving or vitrifying pluripotent stem cells improve cell viability and cell function after thawing. Specifically, functional assaying is directed to determine whether connexin channel inhibitors or pannexin channel inhibitors prevent spontaneous differentiation after thawing, promote expansion of the stem cell cultures and have an effect on induced differentiation toward a specific cell lineage. Finally, it is tested whether application of connexin channel inhibitors or pannexin channel inhibitors during the transportation of pluripotent stem cells after thawing improve the cell viability and the various aspects of stem cell functionality described above.

Example 5

Connexin Channel Inhibition During Hypothermic Conservation of the Heart

Successful heart transplantation not only relies on effective immunosuppressive therapies in the management of transplant survival, but also on refined operative techniques, and efficient donor organ preservation. Although cold preservation helps in limiting organ damage related to warm ischemia, it cannot prevent cold ischemia-related injury.[63] Cold injury of donor organs prior to transplantation is recognized as a major determinant of transplant failure, evidenced by the fact that cold storage time correlates with increased incidence of delayed graft function as well as both acute and chronic rejection of grafts.[64]

Due to its technically simple and easily reproducible nature, cold static preservation is still the current gold standard for myocardial protection in between donor explantation and recipient implantation. Cell stress in hypothermic preservation of heart is in the very first place the consequence of ischemia (as a result of absent blood flow and diffusion-limited transports). Ischemia is of particular interest here because it is one of the strong stimuli leading to the opening of connexin hemichannels. Thus, hemichannel opening is expected to promote cardiomyocyte cell death and gap junctions may spread cell death to neighboring cardiomyocytes. Block of connexin hemichannels in in vivo animal models is associated with a smaller size of induced cardiac infarcts[28] but combining this with block of gap junctions is not possible in vivo because this will lead to potentially fatal arrhythmias due to the central role of gap junctions in electrical conduction of the beating heart. The context of hypothermic conservation creates a clear opportunity to test the combined block of gap junctions and hemichannels and strong protective effects are anticipated. In the atrium, Cx40 and Cx43 are largely expressed while the ventricles mainly express Cx43.[65] A typical experiment consists in testing whether inclusion of connexin channel inhibitors targeting Cx40 and Cx43, in cold storage medium (5° C.) can protect against cardiomyocyte cell death in hearts isolated from laboratory animals. After 5 hours hypothermia, hearts are embedded in paraffin and cut in 5 µm sections to detect dead cells making use of in situ TUNEL staining.

Example 6

Connexin Channel Inhibition During Hypothermic Conservation of the Uterus

Infertility due to the inability of the uterus to carry a pregnancy ranks among the most unresolved issues in reproductive medicine. It affects millions of women worldwide who have congenital or acquired uterine affections, often requiring hysterectomy, and potentially represents a considerable fraction of the general infertile population.[66] Today, uterine factor infertility (UFI) affects 3%-5% of the population. The major groups of women with this type of infertility are those who lack the vagina and the uterus from birth (Mayer-Rokitansky-Küster-Hauser syndrome) or those who have had a hysterectomy as treatment for disease (e.g., cancer). The UFI group also includes women with intrauterine adhesions, most often caused by curettage or infection. The majority of women with UFI have functioning ovaries and thus a chance to become genetic mothers, but they cannot carry their own pregnancies.[67] The only alternatives for women affected by UFI are surrogacy and adoption, options that are not always viable given cultural, religious, legal and personal concerns.[68] Transplantation of the uterus has been suggested as a possible future cure for uterus-factor infertility. Uteri can be obtained from deceased or living donors, e.g., mother-daughter transplant or female-to-male transsexual patients.[69]

One of many aspects that are important for the survival of a transplant is the effect of ischemia and reperfusion, which are inevitable events during the transplantation procedure. During ischemia, tissue is deprived of oxygen and blood nutrients, and this causes a gradual loss of cellular homeostasis. At reperfusion, these changes induce an inflammatory response that can lead to loss of function of the organ. To minimize the ischemic damage and thus the reperfusion injury, lowered temperature is used during storage of the organ to decrease the cellular metabolic and catabolic rate.[67] Cell death can be inhibited by blocking hemichannels and gap junctions during this cold ischemic condition. In the uterus, Cx26 and Cx32 are the major connexins in the endometrium while Cx43 is the predominant connexin subtype in myometrial smooth muscle cells.[70, 71] A typical experiment consists in testing whether inclusion of connexin channel inhibitors targeting Cx26, Cx32 and Cx43, in cold storage medium (5° C.) can protect against cell death in uteri derived from laboratory animals. After 5 hours hypothermia, cell death is evaluated via TUNEL assays on paraffin slices and functionality is tested via isometric tension measurements. This can then be followed up by work on biological uterus material obtained from human living (undergoing transgender surgery) or non-living donors.

REFERENCES

1. Pegg D. E. Principles of cryopreservation. *Methods in molecular biology* 2007; 368:39-57.

2. Bakhach J. The cryopreservation of composite tissues: Principles and recent advancement on cryopreservation of different type of tissues. *Organogenesis* 2009; 5:119-126.
3. Meryman H. T. Cryopreservation of living cells: Principles and practice. *Transfusion* 2007; 47:935-945.
4. Callow A. D. Arterial homografts. *European journal of vascular and endovascular surgery: the official journal of the European Society for Vascular Surgery* 1996; 12:272-281.
5. Vermassen F., A. Deron, H. Janzing, and F. Derom. Immunosuppressive treatment of venous allografts in dogs. The *Journal of thoracic and cardiovascular surgery* 1994; 107:624-626.
6. Vermassen F., N. Degrieck, L. De Kock, J. Goubeau, K. Van Landuyt, L. Noens, and F. Derom. Immunosuppressive treatment of venous allografts. *European journal of vascular surgery* 1991; 5:669-675.
7. Galambos B., L. Csonge, R. von Versen, A. Olah, L. Tamas, and P. Zsoldos. Preservation of vein allograft viability during long-term storage. European surgical research. *Europaische chirurgische Forschung. Recherches chirurgicales europeennes* 2005; 37:60-67.
8. Buckley C. J., S. Abernathy, S. D. Lee, F. R. Arko, D. E. Patterson, and L. G. Manning. Suggested treatment protocol for improving patency of femoral-infrapopliteal cryopreserved saphenous vein allografts. *J. Vasc. Surg.* 2000; 32:731-738.
9. Bujan J., G. Pascual, N. Garcia-Honduvilla, M. J. Gimeno, F. Jurado, A. Carrera-San Martin, and J. M. Bellon. Rapid thawing increases the fragility of the cryopreserved arterial wall. *Eur. J. Vasc. Endovasc.* 2000; 20:13-20.
10. Pascual G., M. Rodriguez, C. Corrales, F. Turegano, N. Garcia-Honduvilla, J. M. Bellon, and J. Bujan. New approach to improving endothelial preservation in cryopreserved arterial substitutes. *Cryobiology* 2004; 48:62-71.
11. Kouzi-Koliakos K., A. Kanellaki-Kyparissi, G. Marinov, E. Tsalie, E. Pavlidou, V. Knyazhev, and D. Kovatchev. Morphological features and apoptosis in the left internal thoracic artery grafts before implantation. *Int. Angiol.* 2007; 26:38-48.
12. Decrock E., M. Vinken, E. De Vuyst, D. V. Krysko, K. D'Herde, T. Vanhaecke, P. Vandenabeele, V. Rogiers, and L. Leybaert. Connexin-related signaling in cell death: To live or let die? *Cell Death Differ.* 2009; 16:524-536.
13. Saez J. C., V. M. Berthoud, M. C. Branes, A. D. Martinez, and E. C. Beyer. Plasma membrane channels formed by connexins: Their regulation and functions. *Physiol. Rev.* 2003; 83:1359-1400.
14. Haefliger J. A., P. Nicod, and P. Meda. Contribution of connexins to the function of the vascular wall. *Cardiovasc. Res.* 2004; 62:345-356.
15. Decrock E., D. V. Krysko, M. Vinken, A. Kaczmarek, G. Crispino, M. Bol, N. Wang, M. De Bock, E. De Vuyst, C. C. Naus, V. Rogiers, P. Vandenabeele, C. Erneux, F. Mammano, G. Bultynck, and L. Leybaert. Transfer of ip3 through gap junctions is critical, but not sufficient, for the spread of apoptosis. *Cell Death Differ.* 2012; 19:947-957.
16. De Vuyst E., N. Wang, E. Decrock, M. De Bock, M. Vinken, M. Van Moorhem, C. Lai, M. Culot, V. Rogiers, R. Cecchelli, C. C. Naus, W. H. Evans, and L. Leybaert. Ca(2+) regulation of connexin 43 hemichannels in c6 glioma and glial cells. *Cell calcium.* 2009; 46:176-187.
17. Retamal M. A., N. Froger, N. Palacios-Prado, P. Ezan, P. J. Saez, J. C. Saez, and C. Giaume. Cx43 hemichannels and gap junction channels in astrocytes are regulated oppositely by proinflammatory cytokines released from activated microglia. *The Journal of neuroscience: the official journal of the Society for Neuroscience* 2007; 27:13781-13792.
18. Retamal M. A., K. A. Schalper, K. F. Shoji, M. V. Bennett, and J. C. Saez. Opening of connexin 43 hemichannels is increased by lowering intracellular redox potential. *Proceedings of the National Academy of Sciences of the United States of America* 2007; 104:8322-8327.
19. De Vuyst E., E. Decrock, M. De Bock, H. Yamasaki, C. C. Naus, W. H. Evans, and L. Leybaert. Connexin hemichannels and gap junction channels are differentially influenced by lipopolysaccharide and basic fibroblast growth factor. *Molecular biology of the cell* 2007; 18:34-46.
20. Thimm J., A. Mechler, H. Lin, S. Rhee, and R. Lal. Calcium-dependent open/closed conformations and interfacial energy maps of reconstituted hemichannels. *J. Biol. Chem.* 2005; 280:10646-10654.
21. Contreras J. E., H. A. Sanchez, L. P. Veliz, F. F. Bukauskas, M. V. Bennett, and J. C. Saez. Role of connexin-based gap junction channels and hemichannels in ischemia-induced cell death in nervous tissue. *Brain research. Brain research reviews* 2004; 47:290-303.
22. Decrock E., E. De Vuyst, M. Vinken, M. Van Moorhem, K. Vranckx, N. Wang, L. Van Laeken, M. De Bock, K. D'Herde, C. P. Lai, V. Rogiers, W. H. Evans, C. C. Naus, and L. Leybaert. Connexin 43 hemichannels contribute to the propagation of apoptotic cell death in a rat c6 glioma cell model. *Cell Death Differ.* 2009; 16:151-163.
23. Kalvelyte A., A. Imbrasaite, A. Bukauskiene, V. K. Verselis, and F. F. Bukauskas. Connexins and apoptotic transformation. *Biochemical pharmacology* 2003; 66:1661-1672.
24. Rodriguez-Sinovas A., J. A. Sanchez, C. Fernandez-Sanz, M. Ruiz-Meana, and D. Garcia-Dorado. Connexin and pannexin as modulators of myocardial injury. *Biochim. Biophys. Acta.* 2012; 1818:1962-1970.
25. MacVicar B. A., and R. J. Thompson. Non-junction functions of pannexin-1 channels. *Trends in neurosciences* 2010; 33:93-102.
26. Chandrasekhar A., and A. K. Bera. Hemichannels: Permeants and their effect on development, physiology and death. *Cell biochemistry and function* 2012; 30:89-100.
27. Decrock E., M. Vinken, M. Bol, K. D'Herde, V. Rogiers, P. Vandenabeele, D. V. Krysko, G. Bultynck, and L. Leybaert. Calcium and connexin-based intercellular communication, a deadly catch? *Cell calcium* 2011; 50:310-321.
28. Wang N., E. De Vuyst, R. Ponsaerts, K. Boengler, N. Palacios-Prado, J. Wauman, C. P. Lai, M. De Bock, E. Decrock, M. Bol, M. Vinken, V. Rogiers, J. Tavernier, W. H. Evans, C. C. Naus, F. F. Bukauskas, K. R. Sipido, G. Heusch, R. Schulz, G. Bultynck, and L. Leybaert. Selective inhibition of cx43 hemichannels by gap19 and its impact on myocardial ischemia/reperfusion injury. *Basic Res. Cardiol.* 2013; 108:309.
29. De Bock M., M. Culot, N. Wang, M. Bol, E. Decrock, E. De Vuyst, A. da Costa, I. Dauwe, M. Vinken, A. M. Simon, V. Rogiers, G. De Ley, W. H. Evans, G. Bultynck, G. Dupont, R. Cecchelli, and L. Leybaert. Connexin channels provide a target to manipulate brain endothelial calcium dynamics and blood-brain barrier permeability. *J. Cerebr. Blood F. Met.* 2011; 31:1942-1957.

30. de Wit C., and T. M. Griffith. Connexins and gap junctions in the edhf phenomenon and conducted vasomotor responses. *Pflugers Archie: European journal of physiology* 2010; 459:897-914.
31. Evans W. H., G. Bultynck, and L. Leybaert. Manipulating connexin communication channels: Use of peptidomimetics and the translational outputs. *J. Membr. Biol.* 2012; 245:437-449.
32. Wang N. DBM, G. Antoons, A. K. Gadicherla, M. Bol., E. Decrock, W. H. Evans, K. R. Sipido, F. F. Bukauskas, and L. Leybaert. Connexin mimetic peptides inhibit cx43 hemichannel opening triggered by voltage and intracellular ca2+ elevation. *Basic Res. Cardiol.* 2012; 107.
33. Davidson J. O., C. R. Green, L. F. Nicholson, S. J. O'Carroll, M. Fraser, L. Bennet, and A. J. Gunn. Connexin hemichannel blockade improves outcomes in a model of fetal ischemia. *Annals of neurology* 2012; 71:121-132.
34. Hawat G., M. Benderdour, G. Rousseau, and G. Baroudi. Connexin 43 mimetic peptide gap26 confers protection to intact heart against myocardial ischemia injury. *Pflug Arch. Eur. J. Phy.* 2010; 460:583-592.
35. Xu H. J., W. L. Chen, Y. Wang, M. Z. Zheng, Y. Y. Chen, and Y. L. Shen. S262a mutation abolishes protective effects of connexin 43 against hypothermic preservation-induced injury in cardiomyocytes. *The Journal of heart and lung transplantation: the official publication of the International Society for Heart Transplantation* 2012; 31:663-669.
36. Bodendiek S. B., and G. Raman. Connexin modulators and their potential targets under the magnifying glass. *Current medicinal chemistry* 2010; 17:4191-4230.
37. Ma W., H. Hui, P. Pelegrin, and A. Surprenant. Pharmacological characterization of pannexin-1 currents expressed in mammalian cells. *The Journal of pharmacology and experimental therapeutics* 2009; 328:409-418.
38. Bol M., C. Van Geyt, S. Baert, E. Decrock, N. Wang, M. De Bock, A. K. Gadicherla, C. Randon, W. H. Evans, H. Beele, R. Cornelissen, and L. Leybaert. Inhibiting connexin channels protects against cryopreservation-induced cell death in human blood vessels. *European journal of vascular and endovascular surgery: the official journal of the European Society for Vascular Surgery* 2013; 45:382-390.
39. Evans W. H., and S. Boitano. Connexin mimetic peptides: Specific inhibitors of gap-junctional intercellular communication. *Biochemical Society transactions* 2001; 29:606-612.
40. Evans W. H., E. De Vuyst, and L. Leybaert. The gap junction cellular internet: Connexin hemichannels enter the signaling limelight. *The Biochemical journal* 2006; 397:1-14.
41. Evans W. H., and L. Leybaert. Mimetic peptides as blockers of connexin channel-facilitated intercellular communication. *Cell communication & adhesion* 2007; 14:265-273.
42. De Vuyst E., E. Decrock, L. Cabooter, G. R. Dubyak, C. C. Naus, W. H. Evans, and L. Leybaert. Intracellular calcium changes trigger connexin 32 hemichannel opening. *The EMBO journal* 2006; 25:34-44.
43. Schwarze S. R., K. A. Hruska, and S. F. Dowdy. Protein transduction: Unrestricted delivery into all cells? *Trends in cell biology* 2000; 10:290-295.
44. Derossi D., G. Chassaing, and A. Prochiantz. Trojan peptides: The penetrating system for intracellular delivery. *Trends in cell biology* 1998; 8:84-87.
45. Lindgren M., M. Hallbrink, A. Prochiantz, and U. Langel. Cell-penetrating peptides. *Trends in pharmacological sciences* 2000; 21:99-103.
46. Muller-Schweinitzer E. Cryopreservation of vascular tissues. *Organogenesis* 2009; 5:97-104.
47. Song Y. C., D. E. Pegg, and C. J. Hunt. Cryopreservation of the common carotid artery of the rabbit—optimization of dimethyl-sulfoxide concentration and cooling rate. *Cryobiology* 1995; 32:405-421.
48. Pant D., L. P. Reynolds, J. S. Luther, P. P. Borowicz, T. M. Stenbak, J. J. Bilski, R. M. Weigl, F. Lopes, K. Petry, M. L. Johnson, D. A. Redmer, and A. T. Grazul-Bilska. Expression of connexin 43 and gap junctional intercellular communication in the cumulus-oocyte complex in sheep. *Reproduction* 2005; 129:191-200.
49. Kolle S., M. Stojkovic, G. Boie, E. Wolf, and F. Sinowatz. Growth hormone-related effects on apoptosis, mitosis, and expression of connexin 43 in bovine in vitro maturation cumulus-oocyte complexes. *Biology of reproduction* 2003; 68:1584-1589.
50. Tong D., T. Y. Li, K. E. Naus, D. Bai, and G. M. Kidder. In vivo analysis of undocked connexin43 gap junction hemichannels in ovarian granulosa cells. *Journal of cell science* 2007; 120:4016-4024.
51. Simon A. M., and D. A. Goodenough. Diverse functions of vertebrate gap junctions. *Trends in cell biology* 1998; 8:477-483.
52. Veitch G. I., J. E. Gittens, Q. Shao, D. W. Laird, and G. M. Kidder. Selective assembly of connexin37 into heterocellular gap junctions at the oocyte/granulosa cell interface. *Journal of cell science* 2004; 117:2699-2707.
53. Balasubramaniyan V., D. K. Dhar, A. E. Warner, W. Y. Vivien Li, A. F. Amiri, B. Bright, R. P. Mookerjee, N. A. Davies, D. L. Becker, and R. Jalan. Importance of connexin-43-based gap junction in cirrhosis and acute-on-chronic liver failure. *Journal of hepatology* 2013; 58:1194-1200.
54. Goncalves L. A., A. M. Vigario, and C. Penha-Goncalves. Improved isolation of murine hepatocytes for in vitro malaria liver stage studies. *Malaria journal* 2007; 6:169.
55. Oyamada M., K. Takebe, A. Endo, S. Hara, and Y. Oyamada. Connexin expression and gap junctional intercellular communication in es cells and ips cells. *Frontiers in pharmacology* 2013; 4:85.
56. Li Y., and T. Ma. Bioprocessing of cryopreservation for large-scale banking of human pluripotent stem cells. *BioResearch open access* 2012; 1:205-214.
57. Reubinoff B. E., M. F. Pera, G. Vajta, and A. O. Trounson. Effective cryopreservation of human embryonic stem cells by the open pulled straw vitrification method. *Human reproduction* 2001; 16:2187-2194.
58. Richards M., C. Y. Fong, S. Tan, W. K. Chan, A. Bongso. An efficient and safe xeno-free cryopreservation method for the storage of human embryonic stem cells. *Stem cells* 2004; 22:779-789.
59. Wong R. C., A. Pebay, L. T. Nguyen, K. L. Koh, and M. F. Pera. Presence of functional gap junctions in human embryonic stem cells. *Stem cells* 2004; 22:883-889.
60. Huettner J. E., A. Lu, Y. Qu, Y. Wu, M. Kim, and J. W. McDonald. Gap junctions and connexon hemichannels in human embryonic stem cells. *Stem cells* 2006; 24:1654-1667.
61. Li Z., K. D. Wilson, B. Smith, D. L. Kraft, F. Jia, M. Huang, X. Xie, R. C. Robbins, S. S. Gambhir, I. L. Weissman, and J. C. Wu. Functional and transcriptional characterization of human embryonic stem cell-derived endothelial cells for treatment of myocardial infarction. *PloS one* 2009; 4:e8443.
62. Ke Q., L. Li, B. Cai, C. Liu, Y. Yang, Y. Gao, W. Huang, X. Yuan, T. Wang, Q. Zhang, A. L. Harris, L. Tao, and A. P. Xiang. Connexin 43 is involved in the generation of human-induced pluripotent stem cells. *Human molecular genetics* 2013; 22:2221-2233.
63. Guan Q. N., S. Y. Li, G. Yip, M. E. Gleave, C. Y. C. Nguan, and C. G. Du. Decrease in donor heart injury by recombinant clusterin protein in cold preservation with University of Wisconsin solution. *Surgery* 2012; 151:364-371.
64. Li S., Q. Guan, Z. Chen, M. E. Gleave, C. Y. Nguan, and C. Du. Reduction of cold ischemia-reperfusion injury by graft-expressing clusterin in heart transplantation. *The Journal of heart and lung transplantation: the official publication of the International Society for Heart Transplantation* 2011; 30:819-826.
65. Severs N. J., A. F. Bruce, E. Dupont, and S. Rothery. Remodelling of gap junctions and connexin expression in diseased myocardium. *Cardiovasc. Res.* 2008; 80:9-19.
66. Grynberg M., J. M. Ayoubi, C. Bulletti, R. Frydman, and R. Fanchin. Uterine transplantation: A promising surrogate to surrogacy? *Ann. N. Y. Acad. Sci.* 2011; 1221:47-53.
67. Wranning C. A., P. Dahm-Kahler, J. Molne, U. A. Nilsson, A. Enskog, and M. Brannstrom. Transplantation of the uterus in the sheep: Oxidative stress and reperfusion injury after short-time cold storage. *Fertil. Steril.* 2008; 90:817-826.
68. Lefkowitz A., M. Edwards, and J. Balayla. The Montreal criteria for the ethical feasibility of uterine transplantation. *Transpl Int.* 2012; 25:439-447.
69. Arora K. S., and V. Blake. Uterus transplantation: Ethical and regulatory challenges. *J. Med. Ethics.* 2013.
70. Lenhart J. A., P. L. Ryan, K. M. Ohleth, and C. A. Bagnell. Expression of connexin-26, -32, and -43 gap junction proteins in the porcine cervix and uterus during pregnancy and relaxin-induced growth. *Biology of reproduction* 1999; 61:1452-1459.
71. Winterhager E., R. Stutenkemper, O. Traub, E. Beyer, and K. Willecke. Expression of different connexin genes in rat uterus during decidualization and at term. *Eur. J. Cell. Biol.* 1991; 55:133-142.

The invention claimed is:

1. A method of protecting a graft, the method comprising: utilizing a connexin channel inhibitor to protect the graft against cell death due to preservation of the graft prior to transplanting the graft into an animal or human patient.

2. The method according to claim 1, wherein said preservation includes cold storage, cryopreservation or vitrification, followed by thawing and/or washing of the graft.

3. The method according to claim 1, wherein said connexin channel inhibitor is able to inhibit both gap junctions and hemichannels.

4. The method according to claim 3, wherein said connexin channel inhibitor is selected from the group consisting of Gap26, Gap27, any combination of Gap26 and Gap27, and Gap26 and/or Gap27 combined with any of the following substances: antibodies directed against connexins, glycyrrhetinic acid, carbenoxolone, heptanol, octanol, halothane, arachidonic acid, oleic acid, oleamide, anandamide, flufenamic acid, niflumic acid, meclofenamic acid, 5-nitro-2-(3-phenyl-propylamino)benzoic acid (NPPB), disodium 4,4'-diisothiocyanatostilbene-2,2'-disulfonate (DIDS), quinine, quinidine, mefloquine, 2-aminoethoxydiphenyl borate (2-APB), spermine, spermidine, triphenylmethanes, triphenylethanes, triarylmethanes, cyclodextrins, the specific connexin hemichannel inhibitors Gap19 and/or Gap24, and the pannexin channel inhibitors $^{10}$Panx1 peptide, probenecid, disodium 4-acetamido-4'-isothiocyanatostilben-2,2'-disulfonate (SITS) and/or (indanyloxyacetic acid) IAA-94.

5. The method according to claim 4, wherein Gap27 is the connexin mimetic inhibitor and has the consensus amino acid sequence $X_1X_2PTEKX_3X_4FX_5X_6$ (SEQ ID NO:1), wherein $X_1$ is S or A, $X_2$ is R or K, $X_3$ is T, N or K, $X_4$ is I, V or L, $X_5$ is I, T, L or M and $X_6$ is I, V, L or Y, or a shortened version of Gap27, wherein the amino acids $X_4FX_5X_6$ or $FX_5X_6$ or $X_5X_6$ or $X_6$ are deleted and/or, wherein Gap26 is the connexin mimetic peptide having the consensus amino acid sequence $X_1CX_2DX_3X_4X_5PX_6SX_7X_8R$ (SEQ ID NO:3), wherein $X_1$ is V, A or I, $X_2$ is Y or F, $X_3$ is K, Q, A, E, H, R, N or D, $X_4$ is S, A, F or Y, $X_5$ is F or A, $X_6$ is I, V or L, $X_7$ is H, N or L and $X_8$ is V, I or R, and/or, wherein said Gap19 is the connexin mimetic peptides having the sequence KQIEIK-KFK (SEQ ID NO:4), and/or, wherein said Gap24 is the connexin mimetic peptides having the sequence GHGDPL-HLEEVKC (SEQ ID NO:5), and/or wherein said $^{10}$Panx1 peptide is the pannexin mimetic peptide having the amino acid sequence WRQAAFVDSY (SEQ ID NO:6).

6. The method according to claim 5, wherein Gap27 is SRPTEKTIFII (SEQ ID NO:2).

7. The method according to claim 4, wherein Gap19, Gap24, or, Gap19 and Gap24 are coupled to a cell internalization sequence.

8. The method according to claim 7, wherein said internalization sequence is YGRKKRRQRRR (SEQ ID NO:7) or RQPKIWFPNRRKPWKK (SEQ ID NO:8).

9. The method according to claim 1, wherein the graft is selected from the group consisting of oocyte, hepatocyte, stem cell, vascular graft, heart and uterus.

10. The method according to claim 9, wherein said vascular graft is a human artery or vein.

11. The method according to claim 10, wherein the vascular graft is selected from the group consisting of aorta, femoral artery, iliac artery, tibial, internal thoracic artery, saphenous vein, and iliac vein.

12. An in vitro method to protect grafts against cell death due to preservation of said grafts, the method comprising:
    a) obtaining a graft from a donor,
    b) adding a protective amount of connexin channel inhibitor to a solution suitable to preserve a graft,
    c) placing said graft into said solution containing said connexin channel inhibitor, and
    d) preserving said graft embedded in said solution containing said connexin channel inhibitor.

13. The in vitro method according to claim 12, wherein said preservation includes cold storage/hypothermia, cryopreservation or vitrification, followed by thawing and washing said graft.

14. The in vitro method according to claim 13, wherein said connexin channel inhibitor is separately added to a solution suitable to wash said previously cryopreserved and thawed graft.

15. The in vitro method according to claim 14, wherein said solution suitable to cryopreserve grafts comprises Hank's Buffered Salt Solution (HBSS), 4-(2-hydroxyethyl)-1-piperazineethanesulfonic acid buffer (HEPES buffer) and dimethylsulfoxide (DMSO) and wherein said solution suitable to wash previously cryopreserved and thawed grafts comprises HBSS and HEPES buffer.

16. The method according to claim 1 that improves the biological function of the graft compared to the biological function of a graft that was not so protected.

17. The method according to claim 3, wherein the connexin mimetic inhibitor is Gap27, which comprises $X_1X_2PTEKX_3X_4FX_5X_6$ (SEQ ID NO:1), wherein
- $X_1$ is S or A,
- $X_2$ is R or K,
- $X_3$ is T, N or K,
- $X_4$ is I, V or L,
- $X_5$ is I, T, L or M, and
- $X_6$ is I, V, L or Y.

18. The method according to claim 3, wherein the connexin mimetic inhibitor comprises $X_1X_2PTEKX_3X_4$ (amino acids 1 through 8 of SEQ ID NO:1) or $X_1X_2PTEKX_3$ (amino acids 1 through 7 of SEQ ID NO:1), wherein
- $X_1$ is S or A,
- $X_2$ is R or K,
- $X_3$ is T, N or K, and
- $X_4$ is I, V or L.

19. The method according to claim 3, wherein the connexin mimetic inhibitor is Gap26, which comprises $X_1CX_2DX_3X_4X_5PX_6SX_7X_8R$ (SEQ ID NO:3), wherein
- $X_1$ is V, A or I,
- $X_2$ is Y or F,
- $X_3$ is K, Q, A, E, H, R, N or D,
- $X_4$ is S, A, F or Y,
- $X_5$ is F or A,
- $X_6$ is I, V or L,
- $X_7$ is H, N or L, and
- $X_8$ is V, I or R.

20. The method according to claim 3, wherein the connexin mimetic inhibitor is Gap19, which comprises KQIEIKKFK (SEQ ID NO:4).

21. The method according to claim 3, wherein the connexin mimetic inhibitor is Gap24, which comprises GHGDPLHLEEVKC (SEQ ID NO:5).

22. The method according to claim 4, wherein $^{10}$Panx1 peptide is the pannexin mimetic peptide, which comprises WRQAAFVDSY (SEQ ID NO:6).

* * * * *